US006960608B2

(12) United States Patent
May et al.

(10) Patent No.: US 6,960,608 B2
(45) Date of Patent: Nov. 1, 2005

(54) FUSED INDAZOLES AND INDOLES AND THEIR USE FOR THE TREATMENT OF GLAUCOMA

(75) Inventors: Jesse A. May, Fort Worth, TX (US); Anura P. Dantanarayana, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 22 days.

(21) Appl. No.: 10/721,204

(22) Filed: Nov. 25, 2003

(65) Prior Publication Data

US 2004/0106597 A1 Jun. 3, 2004

Related U.S. Application Data

(63) Continuation of application No. PCT/US02/17114, filed on May 30, 2002.
(60) Provisional application No. 60/295,428, filed on Jun. 1, 2001.

(51) Int. Cl.$^7$ ...................... A61K 31/415; C07D 23/54; A61P 27/00
(52) U.S. Cl. ...................... 514/405; 514/411; 514/319; 548/359.1
(58) Field of Search ................................ 514/405, 411, 514/319; 548/359.1; 546/203

(56) References Cited

U.S. PATENT DOCUMENTS

| | | | |
|---|---|---|---|
| 4,690,931 A | 9/1987 | Wick et al. | 514/317 |
| 4,985,424 A | 1/1991 | van Wijngaarden et al. | 514/220 |
| 5,151,444 A | 9/1992 | Ueno et al. | 514/530 |
| 5,296,504 A | 3/1994 | Stjernschantz et al. | 514/530 |
| 5,352,708 A | 10/1994 | Woodward et al. | 514/729 |
| 5,385,928 A | 1/1995 | Flaugh | 514/403 |
| 5,422,368 A | 6/1995 | Sternschantz et al. | 514/530 |
| 5,494,928 A | 2/1996 | Bös | 514/415 |
| 5,561,150 A | 10/1996 | Wichmann | 514/406 |
| 5,571,833 A | 11/1996 | Kruse et al. | 514/414 |
| 5,578,612 A | 11/1996 | Macor et al. | 514/323 |
| 5,646,173 A | 7/1997 | Bös et al. | 514/411 |
| 5,874,477 A | 2/1999 | McConnell et al. | 514/530 |
| 5,889,052 A | 3/1999 | Klimko et al. | 514/530 |
| 5,902,815 A | 5/1999 | Olney et al. | 514/285 |
| 6,548,493 B1 | 4/2003 | Robichaud et al. | 514/212.05 |
| 6,552,017 B1 | 4/2003 | Robichaud et al. | 514/219 |
| 6,713,471 B1 | 3/2004 | Robichaud et al. | 514/211.1 |
| 2004/0034015 A1 | 2/2004 | Robichaud et al. | 514/219 |

FOREIGN PATENT DOCUMENTS

| | | |
|---|---|---|
| BE | 718057 | 12/1968 |
| EP | 0771563 A2 | 5/1997 |
| WO | WO 92/20338 | 11/1992 |
| WO | WO 94/13275 | 6/1994 |
| WO | WO 97/33579 | 9/1997 |
| WO | WO 98/18458 | 5/1998 |
| WO | WO 98/31354 | 7/1998 |
| WO | WO 98/56768 | 12/1998 |
| WO | WO 00/12475 | 3/2000 |
| WO | WO 00/12510 | 3/2000 |
| WO | WO 00/16761 | 3/2000 |
| WO | WO 00/35922 | 6/2000 |
| WO | WO 00/44753 | 8/2000 |

OTHER PUBLICATIONS

Osborne, et al. "Do Beta–Adrenoceptors and Serotonin 5–HT$_{1A}$ Receptors Have Similar Functions in the Control of Intraocular Pressure in the Rabbit?" *Ophthalmologica*, vol. 210, pp. 308–314 (1996).

Wang, et al., "Effect of 5–methylurapidil, an $\alpha_{1a}$–adrenergic antagonist and 5–hydroxytryptamine$_{1a}$ agonist, on aqueous humor dynamics in monkeys and rabbits" *Current Eye Research*, vol. 16(8) pp. 769–775 (1997).

IOVS, *Aqueous Humor Dynamics I*, vol. 39(4), S488, 2236–B93 (1998).

Fiorella, "Role of 5–HT$_{2A}$ and 5HT$_{2c}$ receptors in the stimulus effects of hallucinogenic drugs II: reassessment of LSD false positives," *Psychopharmacology*, vol. 121:357–363, 1995.

Clark et al., "Heterocyclic Studies. Part 42. Pyrimido[5,4–d][1,2,3]triazines and some Related Tricyclic Compounds" *J. Chem. Soc., Perkins* vol. 1, pp. 1475–1481 (1984).

Lown et al., "Formation of Novel 1,2–Oxathietanes from 2–Chloroethyl Sulfoxide Precursors and Their Reactions in Solution, Including Formal [σ2s+σ2a] Cycloreversions and Rearrangemetns" *J. Amer. Chem. Soc.*, vol. 108, No. 13, pp. 3811–3818 (1986).

Benson, Jr. et al., "N–Alkyl–5,5–dimethyl–2–oxomorpholin–3–Y1 Radicals. Characterization and Reaction with Molecular Oxygen." *J. Amer. Chem. Soc.* vol. 113, pp. 8879–8886 (1991).

Wentland et al., "Synthesis and Bacterial DNA Gyrase Inhibitory Properties of a Spirocyclopropylquinolone Derivative" *J. Med. Chem.*, vol. 31, pp. 1694–1697 (1988).

Johnson, "Reaction of Aliphatic Amines with Formaldehyde and Nitroparaffins. II. Secondary Amines," *J. Amer. Chem. Soc.*, vol. 68, pp. 12–14 (1946).

Johnson et al., Binding to the Serotonin 5–HT2 Receptor by the Enantiomers of 125$_{I–DOI}$, *Neuropharmacology*, vol. 26, pp. 1803–1806 (1987).

Bowen et al., "Nonlinear regression using spreadsheets," *Trends Pharmacol. Sci.*, vol. 16, pp. 413–417 (1995).

Trondlin, et al. "Der Mechanismus der Indazolsynthese aus o–Toluoldiazoniumsalzen$^2$," *Chem. Ber.*, vol. 111, pp. 367–378 (1978).

(Continued)

*Primary Examiner*—Taofiq Solola
*Assistant Examiner*—Robert Shiao
(74) *Attorney, Agent, or Firm*—Kilyk & Bowersox, P.L.L.C.

(57) ABSTRACT

Novel fused indazoles and indoles are disclosed. Also disclosed are methods for the lowering and controlling of normal or elevated intraocular pressure as well as a method for the treatment of glaucoma using compositions containing one or more of the compounds of the present invention.

6 Claims, No Drawings

OTHER PUBLICATIONS

Bos et al., "Novel Agonists of 5HT2c Receptors. Synthesis and Biological Evaluation of Substituted 2–(Indol–1–yl)–methylethylamines and 2–(Indenol[1,2–b]pyrrol–1–yl)–1–methylethylamines. Improved Therapeutics for Obsessive Compulsive Disorder," J. Med. Chem., vol. 40, pp. 2762–2769 (1997).

Matlin, et al., "6–Diazopenicillanates. Part 1. Reactions with Furans," J. Chem. Soc., Perkin Trans 1, pp. 89–96 (1990).

Griffin et al., "Pharmacological Characterization of an FP Prostaglandin Receptor on Rat Vascular Smoooth Muscle Cells (A7r5) Coupled to Phosphoinositide Turnover and Intracellular Calcuim Mobilization," J. Pharmacol. Expt. Ther. vol. 286, No. 1, pp. 411–418 (1998).

Takahashi et al., "Synthesis of 2–Aryl–3–arylsufonylindoles and 2–Anilino–3–arylsulfonylindoles from 2–(Arylsufony)methylanilines Using the Aza–Wittig Reaction of Iminophosphoranes," Synthesis, pp. 986–990 (1998).

Ruchardt et al., "Durchfuhrung der Jacobsonschen Indazolsynthese im Eintopfverfahren," Liebigs Ann. Chem. pp. 908–927 (1980).

International Search Report for PCT/US02/17114 dated Aug. 23, 2002.

FUSED INDAZOLES AND INDOLES AND THEIR USE FOR THE TREATMENT OF GLAUCOMA

This application is a continuation of International Patent Application No. PCT/US02/17114 filed May 30, 2002 and in turn claims the benefit of U.S. Provisional Patent Application No. 60/295,428 filed Jun. 1, 2001, which is incorporated in its entirety by reference herein.

BACKGROUND OF THE INVENTION

The present invention relates to various indazoles and indoles. These novel compounds are useful for lowering and controlling normal or elevated intraocular pressure (IOP) and for treating glaucoma.

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be at high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

Serotonergic 5-$HT_{1A}$ agonists have been reported as being neuroprotective in animal models and many of these agents have been evaluated for the treatment of acute stroke among other indications. This class of compounds has been mentioned for the treatment of glaucoma (lowering and controlling IOP), see e.g., WO 98/18458 (DeSantis, et al.) and EP 0771563A2 (Mano, et al.). Osborne, et al. (Ophthalmologica, Vol. 210:308–314, 1996) teach that 8-hydroxydipropylaminotetralin (8-OH-DPAT) (a 5-$HT_{1A}$ agonist) reduces IOP in rabbits. Wang, et al. (Current Eye Research, Vol. 16(8):769–775, August 1997, and IVOS, Vol. 39(4), S488, March, 1998) indicate that 5-methylurapidil, an $\alpha_{1A}$ antagonist and 5-$HT_{1A}$ agonist lowers IOP in the monkey, but due to its a1A receptor activity. Also, 5-$HT_{1A}$ antagonists are disclosed as being useful for the treatment of glaucoma (elevated IOP) (e.g., WO 92/0338, McLees). Furthermore, DeSai, et al. (WO 97/35579) and Macor, et al. (U.S. Pat. No. 5,578,612) relate to the use of 5-$HT_1$ and 5-$HT_{1-like}$ agonists for the treatment of glaucoma (elevated IOP). These anti-migraine compounds, e.g., sumatriptan and naratriptan and related compounds, are 5-$HT_{1B,D,E,F}$ agonists.

It has been found that serotonergic compounds which possess agonist activity at 5-$HT_2$ receptors effectively lower and control normal and elevated IOP and are useful for treating glaucoma, see commonly owned co-pending application, PCT/US99/19888, incorporated in its entirety by reference herein. Compounds that act as agonists at 5-$HT_2$ receptors are well known and have shown a variety of utilities, primarily for disorders or conditions associated with the central nervous system (CNS). U.S. Pat. No. 5,494,928 relates to certain 2-(indol-1-yl)-ethylamine derivatives that are 5-$HT_{2C}$ agonists for the treatment of obsessive compulsive disorder and other CNS derived personality disorders. U.S. Pat. No. 5,571,833 relates to tryptamine derivatives that are 5-$HT_2$ agonists for the treatment of portal hypertension and migraine. U.S. Pat. No. 5,874,477 relates to a method for treating malaria using 5-$HT_{2A/2C}$ agonists. U.S. Pat. No. 5,902,815 relates to the use of 5-$HT_{2A}$ agonists to prevent adverse effects of NMDA receptor hypo-function. WO 98/31354 relates to 5-$HT_{2B}$ agonists for the treatment of depression and other CNS conditions. WO 00/12475 relates to indoline derivatives and WO 00/12510 and WO 00/44753 relate to certain indole derivatives as 5-$HT_{2B}$ and 5-$HT_{2C}$ receptor agonists for the treatment of a variety of disorders of the central nervous system, but especially for the treatment of obesity. WO 00/35922 relates to certain pyrazino[1,2-a]quinoxaline derivates as 5-$HT_{2C}$ agonists for the treatment of obsessive compulsive disorder, depression, eating disorders, and other disorders involving the CNS.

WO 00/77002 and WO 00/77010 relate to certain substituted tetracyclic pyrido[4,3-b]indoles as 5-$HT_{2C}$ agonists with utility for the treatment of central nervous system disorders including obesity, anxiety, depression, sleep disorders, cephalic pain, and social phobias among others. Agonist response at the 5-$HT_{2A}$ receptor is reported to be the primary activity responsible for hallucinogenic activity, with some lesser involvement of the 5-$HT_{2C}$ receptor possible [Psychopharmacology, Vol. 121:357, 1995].

U.S. Pat. Nos. 5,561,150 and 5,646,173 relate to certain tricyclic pyrazole derivative compounds which are identified as being 5-$HT_{2C}$ agonists for the treatment of CNS diseases and are primarily directed to lipophilic analogs that have a high probability of entering the brain. Similarly, WO 98/56768 relates to tricyclic 5-$HT_{2C}$ agonists for the treatment of CNS diseases. All the patents, patent applications, and publications mentioned above and throughout are incorporated in their entirety by reference herein and form a part of the present application.

5-Hyroxytryptamine (serotonin) does not cross the blood-brain barrier and enter the brain. However, in order to increase brain serotonin levels the administration of 5-hydroxytryptophan can be employed. The transport of 5-hydroxy-tryptophan into the brain readily occurs, and once in the brain 5-hydroxy-tryptophan is rapidly decarboxylated to provide serotonin.

The chemical synthesis of 2-(4H-pyrrolo[3,2,1-ij]quinolin-1-yl)-ethylamine has been reported [J. Heterocyclic Chem. 11, 387 (1974), Chem. Heterocycl. Compd. (Engl. Transl.) 9, 196 (1973)] with no mention of utility. The synthesis of selected 2-(4H-pyrrolo[3,2,1-ij]quinolin-1-yl)-ethylamine derivatives, such as 2-(8-fluoro-5,6-dihydro-4H-pyrrolo[3,2,1-ij]quinolin-1-yl)-ethylamine, has been reported [Bioorg. Med. Chem. Lett. 10, 919 (2000)]. It was suggested that such compounds could have utility in the treatment of epilepsy and obesity. The preparation of 1- and 2-substituted 2H-indeno[1,2,3-cd]indazoles is disclosed in Belg. 718,057 (1968); these compounds are noted as having psychotherapeutic activity. Various ring substituted amides and esters of 7,8-dihydro-6H-pyrazolo[4,5,1-ij]quinoline-2-carboxylic acid have been disclosed as antagonists at 5-$HT_3$ receptors [U.S. Pat. No. 4,985,424].

Accordingly, there is a need to provide new compounds which avoid the disadvantages described above and which provide increased chemical stability and a desired length of therapeutic activity, for instance, in decreasing intraocular pressure and treating glaucoma.

SUMMARY OF THE PRESENT INVENTION

A feature of the present invention is to provide novel compounds which are 5-HT$_2$ agonists.

Another feature of the present invention is to provide compounds which have increased chemical stability and which are useful in lowering and controlling normal or elevated intraocular pressure and/or treating glaucoma.

Another feature of the present invention is to provide compounds which provide a desired level of therapeutic activity in lowering and controlling normal or elevated intraocular pressure and/or treating glaucoma.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a compound having the Formula I:

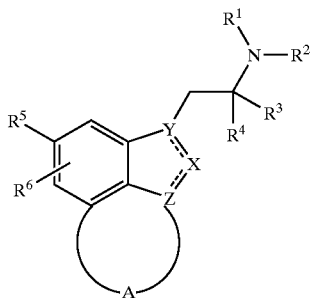

wherein $R^1$ and $R^2$ are independently chosen from hydrogen or an alkyl group such as $C_{1-4}$alkyl;

$R^3$ and $R^4$ are independently chosen from hydrogen, an alkyl group such as $C_{1-4}$alkyl, or $R^3$, $R^4$ and the carbon atom to which they are attached can form a cycloalkyl ring, or furthermore, $R^2$ and $R^3$ together can be $(CH_2)_m$ to form a saturated heterocycle;

$R^5$ is chosen from hydroxyl, an alkoxy group such as $C_{1-4}$alkoxy, an alkyl group such as $C_{1-4}$alkyl, halogen, or $OC(=O)W$;

$R^6$ is chosen from hydrogen, halogen, a unsubstituted or substituted alkyl group such as $C_{1-4}$alkyl or $C_{1-4}$alkyl substituted with halogen;

$R^7$ and $R^8$ are hydrogen or an alkyl group, such as $C_{1-4}$alkyl;

W is an alkyl group such as $C_{1-6}$alkyl, $NR^7R^8$, $N(R^7)CH_2$ $(CH_2)_nN(R^7)(R^8)$, O-alkyl such as $OC_{1-6}$alkyl, a substituted alkyl group such as $C_{1-6}$alkyl (substituted with halogen, hydroxyl, $CO_2C_{1-4}$alkyl, $CON(C_{1-4}$alkyl$)_2$, $C(=NH)NH_2$, $NHC(=NH)NH_2$, or $NH_2$), an alkenyl group such as $C_{2-4}$alkenyl (substituted by phenyl that is unsubstituted or substituted with one or more of an alkyl such as $C_{1-4}$alkyl, an alkoxy such as $C_{1-4}$alkoxy, or halogen);

m is 3 or 4;

n is 2 or 3;

A is selected to complete a 5- to 7-membered ring optionally containing one heteroatom chosen from $NR^7$, O, or S;

X is either N or C;

Y and Z are either N or C, wherein Y and Z cannot be the same; and the dashed bonds denote a suitably appointed single and double bond;

and pharmaceutically acceptable salts and solvates of the compounds of Formula I.

The present invention further relates to pharmaceutical compositions containing at least one compound of Formula I.

The present invention further relates to methods to lower and/or control normal or elevated intraocular pressure by administering an effective amount of a composition containing a compound having Formula I as described above.

The present invention also relates to a method for treating glaucoma which involves administering an effective amount of a composition containing a compound having Formula I as described above.

It is to be understood that both the foregoing general description and the following detailed description are exemplary and explanatory only and are intended to provide a further explanation of the present invention, as claimed.

DETAILED DESCRIPTION OF THE PRESENT INVENTION

The present invention relates to a variety of compounds which are useful according to the present invention. These compounds are generally represented by the following Formula I:

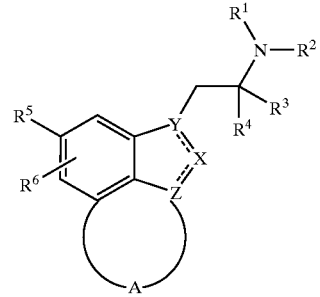

In Formula I, $R^1$ and $R^2$ are independently chosen from hydrogen or an alkyl group such as $C_{1-4}$alkyl;

$R^3$ and $R^4$ are independently chosen from hydrogen, an alkyl group such as $C_{1-4}$alkyl, or $R^3$, $R^4$ and the carbon atom to which they are attached can form a cycloalkyl ring (such as a cyclopropyl ring), or furthermore, $R^2$ and $R^3$ together can be $(CH_2)_m$ to form a saturated heterocycle;

$R^5$ is chosen from hydroxyl, an alkoxy group such as $C_{1-4}$alkoxy, an alkyl group such as $C_{1-4}$alkyl, halogen, or $OC(=O)W$;

$R^6$ is chosen from hydrogen, halogen, a unsubstituted or substituted alkyl group such as $C_{1-4}$alkyl or $C_{1-4}$alkyl substituted with halogen;

$R^7$ and $R^8$ are hydrogen or an alkyl group such as $C_{1-4}$alkyl;

W is an alkyl group such as $C_{1-6}$alkyl, $NR^7R^8$, $N(R^7)CH_2$ $(CH_2)_nN(R^7)(R^8)$, O-alkyl such as $OC_{1-6}$alkyl, a substituted alkyl group such as $C_{1-6}$alkyl (substituted with halogen, hydroxyl, $CO_2C_{1-4}$alkyl, $CON(C_{1-4}$alkyl$)_2$, $C(=NH)NH_2$, $NHC(=NH)NH_2$, or $NH_2$), an alkenyl group such as $C_{2-4}$alkenyl (substituted by phenyl, unsubstituted or substituted with one or more of an alkyl such as $C_{1-4}$alkyl, an alkoxy such as $C_{1-4}$alkoxy or halogen);

m is 3 or 4;
n is 2 or 3;
A represents a 5- to 7-membered ring optionally containing one heteroatom chosen from $NR^7$, O, or S;
X is either N or C;
Y and Z are either N or C, wherein Y and Z are different from each other; and
the dashed bonds denote a suitably appointed single and double bond;
and pharmaceutically acceptable salts and solvates of the compounds of Formula I. Since the treatment of glaucoma is preferably with compounds that do not enter the CNS, relatively polar compounds that are $5-HT_2$ agonists and have incorporated into their structure a phenolic hydroxyl group that can be considered comparable to that of serotonin, are of particular interest.
Preferred Compounds are:
Wherein $R^1$, $R^2$, and $R^3$ are hydrogen;
$R^4$ is $C_{1-4}$alkyl or $R^2$ and $R^3$ together can be $(CH_2)_m$ to form a pyrrolidine;
$R^5$ is chosen from hydroxyl, $C_{1-4}$alkoxy, or OC(=O)W;
$R^6$ is chosen from hydrogen, halogen, $C_{1-4}$alkyl, $C_{1-4}$alkyl substituted with halogen;
$R^7$ and $R^8$ are hydrogen or $C_{1-4}$alkyl;
W is $C_{1-6}$alkyl, $NR^7R^8$, $C_{1-6}$alkyl (which can be substituted with halogen, hydroxyl, $CO_2C_{1-4}$-alkyl;
m is 3;
A is selected to complete a 6-membered ring optionally containing one heteroatom chosen from $NR^7$ or O;
X is either N or C;
Y is N and Z is C; and
the dashed bonds denote a suitably appointed single and double bond;
or pharmaceutically acceptable salts and solvates of the above preferred compounds.
Representative Examples of Preferred Novel Compounds of Formula I are:
2-(2-Aminopropyl)-2,6,7,8-tetrahydro-benzo[cd]indazol-4-ol;
2-(2-Dimethylaminoethyl)-2,6,7,8-tetrahydro-benzo[cd]indazol-4-ol;
2-(2-Aminopropyl)-5-methyl-2,6,7,8-tetrahydro-benzo[cd]indazol-4-ol;
2-(2-Aminopropyl)-5-fluoro-2,6,7,8-tetrahydro-benzo[cd]indazol-4-ol;
2-(6-Fluoro-7-methoxy-4,5-dihydro-3H-benzo[cd]indazol-1-yl)-1-methylethylamine;
Cyclopropanecarboxylic acid 2-(2-aminopropyl)-2,6,7,8-tetrahydro-benzo[cd]indazol-4-yl ester;
1-(2-Aminopropyl)-1,3,4,5-tetrahydro-benzo[cd]indol-7-ol;
1-(2-Aminopropyl)-5H-pyrano[4,3,2-cd]indazol-7-ol; or
1-(2-Aminopropyl)-4-methyl-1,3,4,5-tetrahydro-pyrazolo[4,3,2-de]isoquinolin-7-ol; or
combinations thereof.

It is recognized that compounds of Formula I can contain one or more chiral centers. This invention contemplates all enantiomers, diastereomers and, mixtures thereof.

In the above definitions, the total number of carbon atoms in a substituent group is indicated by the $C_{i-j}$ prefix where the numbers i and j define the number of carbon atoms. This definition includes straight chain, branched chain, and cyclic alkyl or (cyclic alkyl)alkyl groups. A substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

SYNTHESIS

The compounds of Formula I can be prepared by processes analogous to those known in the art. The preparation of compounds 2 of Formula I wherein X is nitrogen or carbon, Y is nitrogen, and Z is carbon can be prepared from the desired fused tricyclic indazole or indole intermediates 1 by methods well known in the art and described in Scheme I [U.S. Pat. No. 5,494,928; J. Med. Chem., Vol. 40:2762, 1997].

Scheme 1

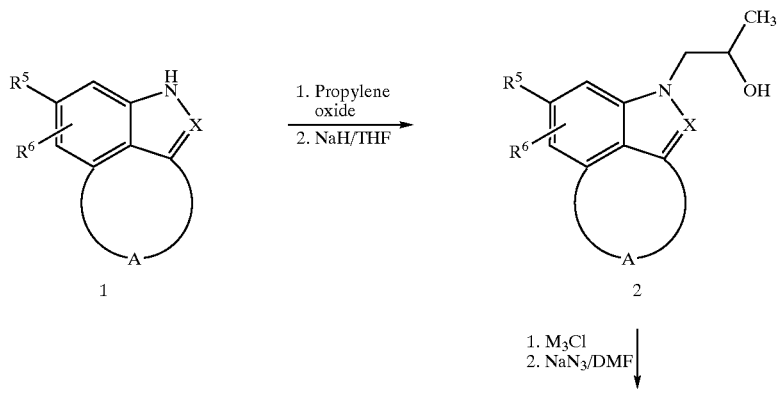

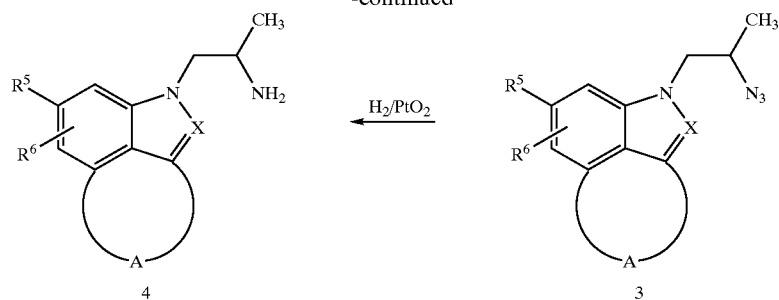

Alternately, and preferably, the compounds 2 can be prepared by the method of Scheme 2. Reaction of 1 with the activated alaninol 5, wherein the hydroxyl group has been suitably activated toward subsequent nucleophilic amination by formation of, for example, a halide or a sulfonate ester [J. Chem. Soc., Perkins Vol. 1:1479, 1981], e.g. methanesulfonyl, toluenesulfonyl, bromophenylsulfonyl, or nitrophenylsulfonyl, provides 6 which following N-deprotection gives compounds 4 of Formula I. Replacement of 5 in Scheme 2 with, for example, an activated sulfonate ester of N-protected (e.g. with t-butyloxycarbonyl, benzyloxycarbonyl) pyrrolidin-3-methanol would, following removal of the amine protective group, provide yet another compound of Formula I. Further, replacement of 5 in Scheme 2 with an activated sulfonate ester of N-(2-hydroxy-1,1-dimethyl-ethyl)-phthalimide [J. Amer. Chem. Soc., Vol. 108:3811, 1986], 2-[(t-butyloxycarbonyl)amino]-2-methylpropanol [J. Amer. Chem. Soc. Vol. 113:8879, 1991], 1-[(t-butyloxycarbonyl)amino]-cyclopropyl-1-methanol [J. Med. Chem., Vol. 31:1694, 1988], or 2-methyl-2-nitro-propan-1-ol [J. Amer. Chem. Soc., Vol. 68:12, 1946] would, following removal of the N-protective groups in the first three cases, or reduction of the nitro group in the latter, provide yet other examples of Formula I. It is evident to those skilled in the art that the aforementioned intermediate compounds 5 contain one chiral center. Therefore compounds 5 can exist as racemates or as one of the two individual and distinct enantiomers which together comprise the racemate. The herewith-defined synthetic procedures are applicable to each of these structural manifestations.

The fused tricyclic indazoles 9 of structure 1 can be prepared from the desired ortho-alkyl-phenyldiazonium salts 8 using appropriate Jacobson indazole synthesis conditions as outlined in Scheme 3 [Synthesis, 1998, 986; Ann. Chem. 1980, 908; Chem. Ber. 111, 367 (1978)]. Substituents G in intermediates 7 can be the same as substituents $R^5$ of compounds 4. However, it can be desirable, because of chemical reactivity or commercial availability of specific synthetic intermediates, that G be a group that can subsequently be transformed to the desired groups $R^5$ by functional group transformations well known to the art. For example, it could be advantageous for G to be a nitro group in 7, which would be converted to a hydroxyl group later in the sequence, for example, at the corresponding compounds 2. Other such functional group transformations may be desirable and would be implemented as required to obtain a specific compound 4.

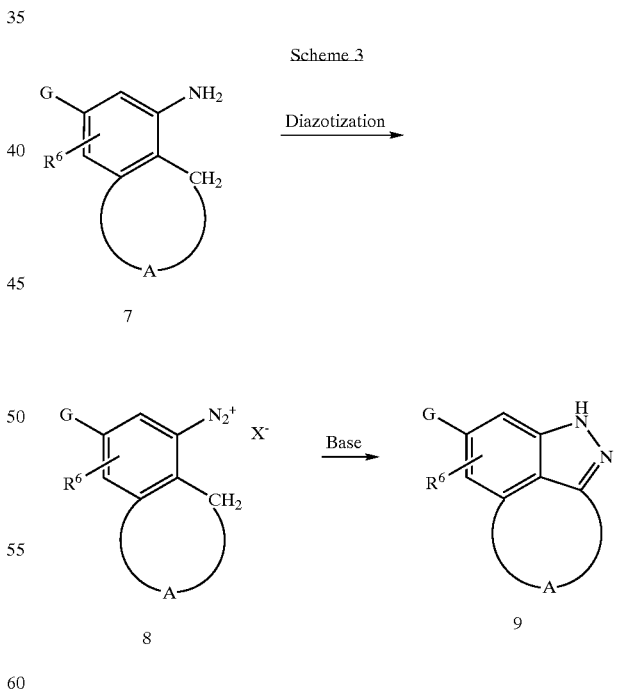

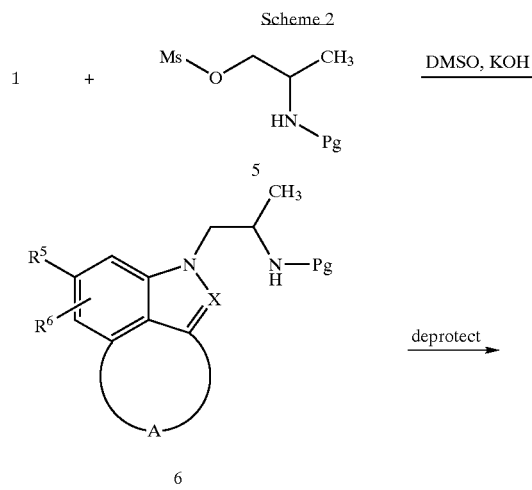

The fused tricyclic indoles 12 of structure 1 can be prepared from the desired ketone 10 via thermolysis of the intermediate vinyl azide 11 (Scheme 4) [*J. Chem. Soc., Perkin Trans* 1, 1990, 89)].

Scheme 4

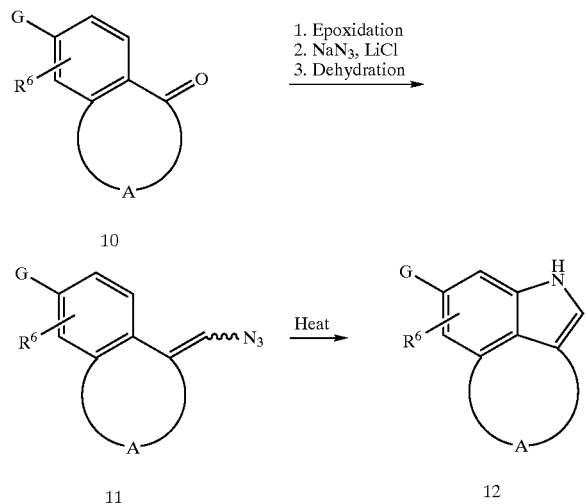

Compounds of Formula I, wherein $R^5$ is OC(=O)W, can be prepared by reacting the appropriate compound 4, such as 13, or preferably a suitable amino-protected intermediate, e.g. 14 (Scheme 5) with the desired activated acid derivative, such as an acid halide or active ester, or the like, to provide the esters 15. Removal of the N-protective group from the intermediate 15 provides the desired compounds 16 of Formula I.

Scheme 5

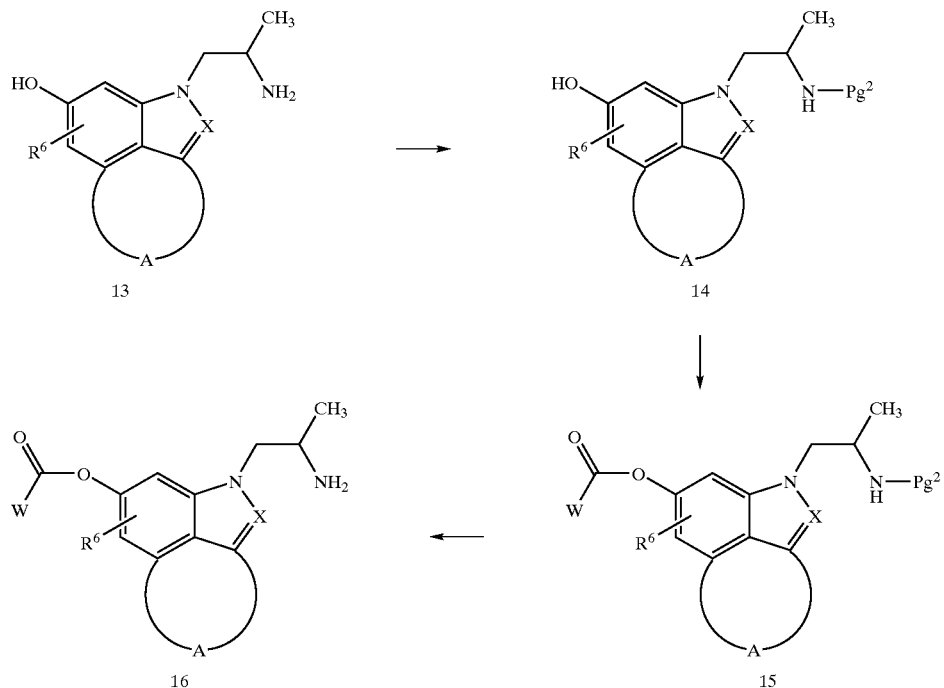

The compounds of the present invention can be used to lower and control IOP including IOP associated with normotension glaucoma, ocular hypertension, and glaucoma in warm blooded animals including humans. The compounds are preferably formulated in pharmaceutical compositions which are preferably suitable for topical delivery to the eye of the patient.

The compounds of this invention, Formula 1, can be incorporated into various types of pharmaceutical compositions, such as ophthalmic formulations for delivery to the eye (e.g., topically, intracamerally, or via an implant). The compounds are preferably incorporated into topical ophthalmic formulations for delivery to the eye. The compounds may be combined with ophthalmologically acceptable preservatives, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8. The compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), $\alpha_1$ antagonists (e.g., nipradolol), $\alpha_2$ agonists (e.g. iopidine and brimonidine), miotics (e.g., pilocarpine and epinephrine), prostaglandin analogs (e.g., latanoprost, travaprost, unoprostone, and compounds set forth in U.S. Pat. Nos. 5,889,052; 5,296,504; 5,422,368; and 5,151,444, "hypotensive lipids" (e.g., lumigan and compounds set forth in 5,352,708), and neuroprotectants (e.g., compounds from U.S. Pat. No. 4,690,931, particularly eliprodil and R-eliprodil, as set forth in a pending application U.S. Ser. No. 06/203,350, and appropriate compounds from WO 94/13275, including memantine.

In the formulas described above, the alkyl group can be straight-chain, branched or cyclic and the like. Halogen includes Cl, Br, F, or I. Alkoxy is understood as an alkyl group bonded through an oxygen atom.

The compounds of the present invention preferably function as 5-HT$_2$ agonists and preferably do not enter the CNS. In more detail, the particular compounds of the present invention have incorporated into their structure a phenolic hydroxyl group which is considered comparable to that of serotonin and thus the compounds of the present invention preferably do not cross the blood-brain barrier and enter the brain. Compounds having the ability to be a 5-HT$_2$ agonist are beneficial for controlling IOP as well as the treatment of glaucoma as shown in International Published Patent Application No. WO 00/16761, incorporated in its entirety by reference herein.

The compounds of the present invention preferably provide increased chemical stability and preferably achieve the desired level of therapeutic activity which includes a lowering or controlling of IOP.

The compounds of the present invention can be used in controlling or lowering IOP in warm blooded animals including humans. Preferably, an effective amount of the compound is administered to the patient such that the IOP is controlled or lowered to acceptable levels. Furthermore, the compounds of the present invention can be used to treat glaucoma in warm blooded animals, including humans, by administering an effective amount of the compound to a patient in need of such treatment to treat the glaucoma.

In another embodiment of the present invention, the present invention relates to a method to activate serotonin receptors and involves administering at least one compound of the present invention to a patient in an amount effective to activate serotonin receptors, such as the dosage levels described herein.

The following Examples are given to illustrate the preparation of compounds that are the subject of this invention but should not be construed as implying any limitations to the claims.

The preferred compound of Formula I is described in Example 1. The proton magnetic resonance spectrum of each compound of the Examples was consistent with the assigned structure.

METHOD 1

5-HT$_2$ Receptor Binding Assay

To determine the affinities of serotonergic compounds at the 5-HT2 receptors, their ability to compete for the binding of the agonist radioligand [$^{125}$I]DOI to brain 5-HT$_2$ receptors is determined as described below with minor modification of the literature procedure [Neuropharmacology, 26, 1803 (1987)]. Aliquots of post mortem rat or human cerebral cortex homogenates (400 μL) dispersed in 50 mM Tris HCl buffer (pH 7.4) are incubated with [$^{125}$I]DOI (80 μM final) in the absence or presence of methiothepin (10 μM final) to define total and non-specific binding, respectively, in a total volume of 0.5 mL. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the IC$_{50}$ or Ki value.

METHOD 2

5-HT$_2$ Functional Assay: Phosphoinositide (PI) Turnover Assay

The relative agonist activity of serotonergic compounds at the 5-HT$_2$ receptor can be determined in vitro using the ability of the compounds to stimulate the production of [$^3$H]inositol phosphates in [$^3$H]myo-inositol-labeled A7r5 rat vascular smooth muscle cells by their ability to activate the enzyme phospholipase C. These cells are grown in culture plates, maintained in a humidified atmosphere of 5% CO$_2$ and 95% air and fed semi-weekly with Dulbecco's modified Eagle medium (DMEM) containing 4.5 g/L glucose and supplemented with 2 mM glutamine, 10 μg/ml gentamicin, and 10% fetal bovine serum. For the purpose of conducting the phosphoinositide (PI) turnover experiments, the A7r5 cells are cultured in 24-well plates as previously [J. Pharmacol. Expt. Ther. 286, 411 (1998)]. Confluent cells are exposed for 24–30 hrs to 1.5 μCi [$^3$H]-myo-inositol (18.3 Ci/mmol) in 0.5 mL of serum-free medium. Cells are then rinsed once with DMEM/F-12 containing 10 mM LiCl prior to incubation with the test agent (or solvent as the control) in 1.0 mL of the same medium for 1 hr at 37° C., after which the medium is aspirated and 1 mL of cold 0.1 M formic acid added to stop the reaction. The chromatographic separation of [$^3$H]-inositol phosphates ([$^3$H]-IPs) on an AG-1-X8 column is performed as previously described [J. Pharmacol. Expt. Ther. 286, 411 (1998)] with sequential washes with H$_2$O and 50 mM ammonium formate, followed by elution of the total [$^3$H]-IPs fraction with 1.2 M ammonium formate containing 0.1 M formic acid. The eluate (4 mL) is collected, mixed with 15 ml scintillation fluid, and the total [$^3$H]-IPs determined by scintillation counting on a beta-counter. Concentration-response data are analyzed by the sigmoidal fit function of the Origin Scientific Graphics software (Microcal Software, Northampton, MA) to determine agonist potency (EC$_{50}$ value) and efficacy (E$_{max}$). Serotonin (5-HT) is used as a positive control (standard) agonist compound and the efficacy of test compounds is compared to that of 5-HT (set at 100%). The concentration of the compound needed to stimulate the production of [$^3$H]-IPs by 50% of the maximum response is termed the EC$_{50}$ value.

The above procedures were used to generate the data shown in Table 1.

TABLE 1

5-HT$_2$ Receptor Binding and Functional Data

| Compound | IC$_{50}$, nM | EC$_{50}$, nM | Efficacy (E$_{max}$, %) |
|---|---|---|---|
| Example 1 | 0.714 | 374 | 85 |
| Example 2 | 9.62 | 1440 | 55 |
| 5-HT | 0.941 | 469 | 100 |

METHOD 3

Acute IOP Response in Lasered (Hypertensive) Eyes of Conscious Cynomolgus Monkeys Intraocular pressure (IOP) was determined with an Alcon Pneumatonometer after light corneal anesthesia with 0.1% proparacaine. Eyes were washed with saline after each measurement. After a baseline IOP measurement, test compound was instilled in one 30 μL aliquot to the right eyes only of nine cynomolgus monkeys. Vehicle was instilled in the right eyes of six additional animals. Subsequent IOP measurements were taken at 1, 3, and 6 hours. A compound is considered efficacious in this model of ocular hypertension if there is a decrease in the baseline IOP of the lasered eye (O.D.) of at least 20% following topical administration.

The Profile of the IOP Response Following Topical Administration of Representative Compounds is Provided in Table 2

TABLE 2

IOP Response in Conscious Cynomolgus Monkeys

| Compound | Dose, μg | Baseline IOP (mmHg) | Percent Change in IOP ± SEM Hours after Dose | | |
|---|---|---|---|---|---|
| | | | 1 | 3 | 6 |
| Example 1 | 300 | 34.3 | −5.9 ± 2.69 | −20.0 ± 3.54 | −21.6 ± 4.91 |
| Vehicle Control | — | 34.7 | −4.6 ± 3.09 | 1.20 ± 1.80 | 2.10 ± 7.57 |

EXAMPLE 1

2-(2-Aminopropyl)-2,6,7,8-tetrahydro-benzo[cd]indazol-4-ol dihydrochloride

Step A: 3-Nitro-5,6,7,8-tetrahydro-naphthalen-1-ylamine and 2-Nitro-5,6,7,8-tetrahydronaphthalen-1-ylamine To a solution of 1-amino-5,6,7,8-tetrahydronapthalene (13.0 g, 88.0 mmol) in concentrated sulfuric acid (80 mL) at 0° C. was added a solution of sodium nitrite (8.3 g, 97.0 mmol) in concentrated sulfuric acid (60 mL) also at 0° C. over 30 min and the resultant dark solution was stirred at this temperature for 3 h. The reaction mixture was added to ice and basified with a saturated solution of sodium hydroxide. This mixture was extracted with ethyl acetate (4×200 mL) and the combined extracts were washed with brine, dried (MgSO4), and evaporated to a residue that was purified by column chromatography (silica, 20% to 30% ethyl acetate in hexane) to give two products: 3-nitro-5,6,7,8-tetrahydro-naphthalen-1-ylamine (7.5 g, 44%) [MS (ES) m/z 192 (M$^+$); $^1$H NMR (CDCl$_3$) δ 7.39(1H, d, J=2.0 Hz), 7.31(1H, d, J=2.0 Hz), 3.84 (2H, brs), 2.82 (2H, t, J=6.0 Hz), 2.48 (2H, t, J=6.0 Hz), 1.81 (2H, m)] and 2-nitro-5,6,7,8-tetrahydro-naphthalen-1-ylamine (3.7 g, 22%) [MS (ES) m/z 192 (M$^+$); $^1$H NMR (CDCl$_3$) δ 7.85 (1H, d, J=8.0 Hz), 6.52 (1H, d, J=8.0 Hz), 4.17 (2H, brs), 3.06 (2H, t, J=6.0 Hz), 2.44 (2H, t, J=6.0 Hz), 1.84 (2H, m)].

Step B: 7-Nitro-1,3,4,5-tetrahydro-benzo[cd]indazole

To a solution of 3-nitro-5,6,7,8-tetrahydro-naphthalen-1-ylamine (5.9 g, 31.0 mmol) prepared in Step A in glacial acetic acid (100 mL) was added a solution of sodium nitrite (2.13 g, 31.0 mmol) in water (5.0 mL) at 0° C., and the resultant dark solution was stirred at this temperature for 20 h. The volatiles were evaporated and the residue was basified with a saturated solution of sodium bicarbonate (100 mL). The aqueous was extracted with ethyl acetate (4×200 mL) and the combined extracts were washed with brine, dried (MgSO4) and evaporated to a residue that was purified by column chromatography (silica, 20% to 30% gradient of ethyl acetate in hexane) to give an oil (3.8 g, 60%): MS (ES) m/z 204 (M$^+$); $^1$H NMR (CDCl$_3$) δ 8.22 (1H,s), 7.77 (1H, s), 3.06 (4H, m), 2.26 (2H, m).

Step C: 1-(7-Nitro-4,5-dihydro-3H-benzo[cd]indazol-1-yl)-propan-2-ol

To a solution of the product from Step B (4.85 g, 23.9 mmol) in ethanol (50 mL) was added sodium ethoxide (14.2 mL, 35.0 mmol, 21% solution in ethanol) at room temperature. After 30 min, propylene oxide (4.14 mL, 47.8 mmol) was added, and the resultant solution was stirred for 18 h at room temperature. A saturated aqueous ammonium chloride solution (20 mL) was added to the reaction mixture and the ethanol was evaporated. This mixture was extracted with ethyl acetate (3×65 mL) and the combined extracts were washed with brine (30 mL), dried (MgSO$_4$), and evaporated. The residue was purified by column chromatography (silica, 50% to 80% gradient of ethyl acetate in hexane) to yield the desired product as a solid (2.0 g, 32%): m.p: 147–148° C.; MS (ES) m/z 262 (M$^+$); $^1$H NMR (CDCl$_3$) δ 8.17 (1H, s), 7.74 (1H, s), 4.31 (3H, m), 3.05 (4H, 2d, J=6.0 Hz), 2.19 (4H, m), 1.30 (3H, t, J=6.0 Hz). The regioisomer formed during the alkylation was also isolated as a solid (1.4 g, 22%): mp 140–141° C.

Step D: 1-(7-Amino-4,5-dihydro-3H-benzo[cd]indazol-1-yl)-propan-2-ol

To a solution of the product from Step C (2.0, 7.6 mmol) in ethanol was added Pd/C (10%, 0.10 g) and the resultant suspension was stirred under a hydrogen atmosphere for 20 h at room temperature. The reaction mixture was filtered through a filter-aide and the filtrate was concentrated to yield a solid (1.7 g, 97%): m.p: 125–127° C.; MS (ES) m/z 232 (M$^+$); $^1$H NMR (CDCl$_3$) δ 6.27 (2H, s), 4.31–3.93 (3H, m), 2.93–2.78 (4H, m), 2.14 (2H, m) 1.25 (3H, t, J=6.0 Hz).

Step E: 2-(2-Hydroxypropyl)-2,6,7,8-tetrahydro-benzo[cd]indazol-4-ol

The product from Step D (1.90 g, 8.4 mmol) was dissolved in H$_2$SO$_4$/H$_2$O (1:2, 60 mL) and cooled to 0° C. A solution of NaNO$_2$ (0.64 g, 9.2 mmol) in H$_2$O (2.0 mL) was added dropwise and the resultant dark solution was stirred for 2 h. Water (40 mL) was added to this solution and the mixture was heated to 110° C. for 2 h. After cooling the mixture to room temperature it was carefully neutralized with a saturated aqueous NaHCO$_3$ solution and extracted with ethyl acetate (3×65 mL). The combined extracts were washed with brine (10 mL), dried (MgSO$_4$) and evaporated to a residue which was purified by column chromatography (silica, 50% to 60% gradient of ethyl acetate in hexane) to give a solid (1.2 g, 83%): m.p: 153–155° C.; MS (ES) m/z 233(M$^+$); $^1$H NMR (CDCl$_3$) δ 9.39 (1H, s), 6.50 (1H, s), 6.34 (1H, s), 4.84 (1H, d, J=4.0 Hz), 4.00 (3H, m), 2.76 (2H, q, j=6.0 Hz), 2.01 (2H, m), 1.01 (3H, d, J=6.0 Hz).

Step F: 1-(7-Benzyloxy-4,5-dihydro-3H-benzo[cd]indazol-1-yl)-propan-2-ol

To a stirred solution of the product from Step E (1.2 g, 5.2 mmol) in ethanol (20 mL) was added $K_2CO_3$ (0.86 g, 6.3 mmol) followed by benzyl bromide (0.74 mL, 6.3 mmol) at room temperature. The resultant dark solution was heated at reflux for 4 h. Solvent was evaporated, the residue was diluted with 2 N HCl (60 mL), and this solution was extracted with ethyl acetate (3×50 mL). The combined extracts were washed with brine (30 mL), dried, and evaporated to a residue which was purified by column chromatography (silica, 40% ethyl acetate in hexane) to give an oil (0.79 g, 47%): MS (ES) m/z 232 ($M^+$); $^1H$ NMR (CDCl$_3$) δ 7.32 (5H, m), 6.60 (1H, s), 6.59 (1H, s), 5.29 (2H, s), 4.31 (2H, m), 4.19 (1H, m), 2.90 (2H, m), 2.11 (2H, m), 1.21 (3H, d, J=6.0 Hz).

Step G: 1-(2-Azidopropyl)-7-benzyloxy-1,3,4,5-tetrahydro-benzo[cd]indazole

To a stirred solution of the product from Step F (0.77 g, 2.4 mmol) in dichloromethane (10 mL) was added triethylamine (0.40 mL, 2.9 mmol) followed by methanesulfonyl chloride (0.22 mL, 2.9 mmol) at 0° C. After 30 min, dichloromethane (50 mL) was added followed by water (50 mL). The organic layer was separated and the aqueous was extracted with dichloromethane (2×50 mL). The combined extracts were washed with brine (30 mL), dried (MgSO4), and evaporated to a residue that was taken up in DMF (6 mL) and sodium azide (0.33 g, 5.0 mmol) was added. The reaction mixture was heated at 70° C. for 17 h, poured into water, and extracted with ether (3×50 mL). The combined extracts were washed with brine, dried (MgSO4), and evaporated to a residue that was purified by column chromatography (silica, hexane to 10% ethyl acetate in hexane) to give an oil (0.75 g, 90%): MS (ES) m/z 348 ($M^+$).

Step H: 2-(2-Aminopropyl)-2,6,7,8-tetrahydro-benzo[cd]indazol-4-ol

To a solution of the product from Step G (0.74 g, 2.2 mmol) in ethanol under a nitrogen atmosphere at room temperature was added Pd/C (10%, 0.10 g) followed by ammonium formate (0.54 g, 8.5 mmol). This suspension was stirred for 24 h at room temperature followed by filtration through a filter-aide. The filtrate was evaporated to a residue that was purified by column chromatography (silica, 5% to 20% gradient of methanol in dichloromethane) to give a solid that was converted to the dihydrochloride salt, which was crystallized from methanol/ether (0.38 g, 58%): m.p 286–288° C.; MS (ES) m/z 232 ($M^+$); $^1H$ NMR (DMSO-d$_6$) δ 8.28 (3H, brs), 6.59 (1H, s), 6.43 (1H, s), 4.40–4.22 (2H, m), 3.61 (11H, m), 2.79 (4H, m), 2.27 (2H, m), 1.18 (3H, d, J=8.0 Hz).

Analysis. Calculated for $C_{13}H_{17}N_3O \cdot 2HCl \cdot 0.2H_2O$: C, 50.73; H, 6.35; N, 13.65. Found: C, 50.44; H, 6.40; N, 13.45.

EXAMPLE 2

2-(2-Aminopropyl)-2,6,7,8-tetrahydro-benzo[cd]indazol-3-ol dihydrochloride

Step A: 8-Nitro-1,3,4,5-tetrahydro-benzo[cd]indazole

A solution of 2-nitro-5,6,7,8-tetrahydro-naphthalen-1-ylamine (6.0 g, 31.4 mmol) in glacial acetic acid (50 mL) was treated as described in Step B of Example 1 to give an oil (5.2 g, 82%): MS (ES) m/z 202 (M–H)—.

Step B: 1-(8-Nitro-4,5-dihydro-3H-benzo[cd]indazol-1-yl)-propan-2-ol

A solution of the product from Step A (3.5 g, 17.2 mmol) in ethanol (50 mL) was treated as described in Step C of Example 1 to provide a solid (0.90 g, 20%): m.p 151–152° C.; MS (ES) m/z 262($M^+$); $^1H$ NMR (CDCl$_3$) δ 8.21(1H, d, J=8.0 Hz), 7.73 (1H, d, J=8.0 Hz), 4.32 (2H, m), 3.45 (2H, t, J=6.0 Hz), 3.01(2H, t, J=6.0 Hz), 2.19 (2H, m), 1.29 (3H, J=6.0 Hz). The regioisomer formed during the alkylation was also isolated (0.60 g, 13%): mp 144–146° C.

Step C: 1-(8-Amino-4,5-dihydro-3H-benzo[cd]indazol-1-yl)-propan-2-ol

A solution of the product from Step B (0.85, 3.3 mmol) in ethanol was treated as described for Step D of Example 1 to provide a solid (0.71 g, 99%): m.p 129-131° C.; MS (ES) m/z 232 ($M^+$); $^1H$ NMR (DMSO-d$_6$) δ 7.03 (1H, d, J=8.0 Hz), 6.72 (1H, d, J=8.0 Hz), 4.80 (1H, d, J=4.0 Hz), 4.51(2H, brs), 4.01 (3H, m), 2.78 (2H, t, J=6.0 Hz), 2.62 (2H, t, J=6.0 Hz), 2.02 (2H, m), 1.00 (3H, d, J=6.0 Hz).

Step D: 2-(2-Hydroxypropyl)-2,6,7,8-tetrahydro-benzo[cd]indazol-3-ol

The product from Step C (0.70 g, 3.2 mmol) was dissolved in $H_2SO_4/H_2O$ (1:2, 30 mL) and treated as described in Step E of Example 1 to provide a solid (0.60 g, 86%): m.p 162-163° C.; MS (ES) m/z 233($M^+$).

Step E: 1-(8-Benzyloxy-4,5-dihydro-3H-benzo[cd]indazol-1-yl)-propan-2-ol

A solution of the product from Step D (0.59 g, 2.6 mmol) in ethanol (20 mL) was treated as described in Step F of Example 1 to provide a solid (0.46 g, 54%): m.p 95–97° C.; MS (ES) m/z 323 ($M^+$); $^1H$ NMR (CDCl3) δ 7.34 (5H, m), 7.14 (1H, s), 5.08 (2H, s), 4.31 (2H, m), 4.13 (2H, m), 3.02 (5H, m), 2.19 (3H, m), 1.27(3H, t, J=6.0 Hz).

Step F: 1-(2-Azidopropyl)-8-benzyloxy-1,3,4,5-tetrahydro-benzo[cd]indazole

A solution of the product from Step E (0.46 g, 1.4 mmol) in dichloromethane (10 mL) was treated as described for Step G of Example 1 to provide an oil (0.20 g, 42%): MS (ES) m/z 348 ($M^+$).

Step G: 2-(2-Aminopropyl)-2,6,7,8-tetrahydro-benzo[cd]indazol-3-ol dihydrochloride A solution of the product from Step F (0.19, 0.54 mmol) in ethanol was treated as described in Step H of Example 1 to provide the dihydrochloride salt (0.10 g, 62%): m.p 284–286° C.; MS (ES) m/z 232 ($M^+$); $^1H$ NMR (DMSO-d$_6$) δ 8.29 (3H, brs), 7.21 (1H, d, J=6.0 Hz), 6.94 (1H, d, J=6.0 Hz), 4.48 (2H, m), 3.61 (1H,m), 2.79 (4H, m), 2.00 (2H, m), 1.16(3H,d,J=6.0 Hz).

Analysis. Calculated for $C_{13}H_{17}N_3O \cdot 2HCl$: C, 51.33; H, 6.30; N, 13.81. Found: C, 51.41; H, 6.34; N, 13.67.

EXAMPLE 3

| Ingredients | Amount (wt %) |
|---|---|
| 2-(2-Amino-propyl)-2,6,7,8-tetrahydro-benzo[cd]indazol-4-ol dihydrochloride | 0.01–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |
| Purified water | q.s. to 100% |

EXAMPLE 4

| Ingredients | Amount (wt %) |
|---|---|
| 2-(2-Amino-propyl)-2,6,7,8-tetrahydro-benzo[cd]indazol-4-ol dihydrochloride | 0.01–2% |

-continued

| Ingredients | Amount (wt %) |
| --- | --- |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |
| Purified water | q.s. to 100% |

EXAMPLE 5

| Ingredients | Amount (wt %) |
| --- | --- |
| 2-(2-Amino-propyl)-2,6,7,8-tetrahydro-benzo[cd]indazol-4-ol dihydrochloride | 0.01–2% |
| Guar gum | 0.4–6.0% |
| Dibasic sodium phosphate (anhydrous) | 0.2%- |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH |
| Purified water | q.s. to 100% |

EXAMPLE 6

| Ingredients | Amount (wt %) |
| --- | --- |
| 2-(2-Amino-propyl)-2,6,7,8-tetrahydro-benzo[cd]indazol-4-ol dihydrochloride | 0.01–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting Ph |

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A compound represented by Formula I:

wherein $R^1$ and $R^2$ are independently chosen from hydrogen or an alkyl group;

$R^3$ and $R^4$ are independently chosen from hydrogen, an alkyl group or $R^3$, $R^4$ and the carbon atom to which they are attached form a cycloalkyl ring;

$R^5$ is chosen from hydroxyl, alkoxy, alkyl, halogen, or $OC(=O)W$;

$R^6$ is chosen from hydrogen, halogen, a substituted or unsubstituted alkyl group;

$R^7$ and $R^8$ are hydrogen or an alkyl group;

W is a substituted or unsubstituted alkyl group, $NR^7R^8$, $N(R^7)CH_2(CH_2)_nN(R^7)(R^8)$, O-alkyl, or a substituted or unsubstituted alkenyl;

m is 3 or 4;

n is 2 or 3;

A is a 6-membered ring containing 6 carbon atoms;

X is N; Y is N; Z is C; and the dashed bonds denote a suitably appointed single and double bond;

or pharmaceutically acceptable salts or solvates thereof.

2. The compound of claim 1, wherein $R^1$ and $R^2$ are independently chosen from hydrogen or $C_{1-4}$alkyl;

$R^3$ and $R^4$ are independently chosen from hydrogen, $C_{1-4}$alkyl or $R^3$, $R^4$ and the carbon atom to which they are attached form a cyclopropyl ring;

$R^5$ is chosen from hydroxyl, $C_{1-4}$alkoxy, $C_{1-4}$alkyl, halogen, or $OC(=O)W$;

$R^6$ is chosen from hydrogen, halogen, $C_{1-4}$alkyl, $C_{1-4}$alkyl substituted with halogen;

$R^7$ and $R^8$ are hydrogen or $C_{1-4}$alkyl;

W is $C_{1-6}$alkyl, $NR^7R^8$, $N(R^7)CH_2(CH_2)_nN(R^7)(R^8)$, $OC_{1-6}$alkyl, $C_{1-6}$alkyl optionally substituted with halogen, hydroxyl, $CO_2C_{1-4}$alkyl, $CON(C_{1-4}$alkyl$)_2$, $C(=NH)NH_2$, $NHC(=NH)NH_2$, or $NH_2$, $C_{2-4}$alkenyl optionally substituted by phenyl, unsubstituted or substituted with one or more of $C_{1-4}$alkyl, $C_{1-4}$alkoxy or halogen;

m is 3 or 4;

n is 2 or 3;

A is a 6-membered ring containing 6 carbon atoms;

X is N; Y is N; Z is C; and the dashed bonds denote a suitably appointed single and double bond;

or pharmaceutically acceptable salts or solvates thereof.

3. The compound of claim 1, wherein said $R^3$ and $R^4$ together form a cycloalkyl ring.

4. The compound of claim 1, wherein $R^1$, $R^2$, and $R^3$ are hydrogen;

$R^4$ is $C_{1-4}$alkyl;

$R^5$ is chosen from hydroxyl, $C_{1-4}$alkoxy, or $OC(=O)W$;

$R^6$ is chosen from hydrogen, halogen, $C_{1-4}$alkyl, $C_{1-4}$alkyl substituted with halogen;

$R^7$ and $R^8$ are hydrogen or $C_{1-4}$alkyl;

W is $C_{1-6}$alkyl, $NR^7R^8$, $C_{1-6}$alkyl optionally substituted with halogen, hydroxyl, or $CO_2C_{1-4}$alkyl;

m is 3;

A is a 6-membered ring containing 6 carbon atoms;

X is N;

Y is N and Z is C; and the dashed bonds denote a suitably appointed single and double bond.

5. The compound of claim 1, wherein the compound is:
2-(2-Aminopropyl)-2,6,7,8-tetrahydro-benzo[cd]indazol-4-ol;

2-(2-Dimethylaminoethyl)-2,6,7,8-tetrahydro-benzo[cd]
   indazol-4-ol;
2-(2-Aminopropyl)-5-methyl-2,6,7,8-tetrahydro-benzo
   [cd]indazol-4-ol;
2-(2-Aminopropyl)-5-fluoro-2,6,7,8-tetrahydro-benzo
   [cd]indazol-4-ol;
2-(6-Fluoro-7-methoxy-4,5-dihydro-3H-benzo[cd]
   indazol-1-yl)-1-methylethylamine;

Cyclopropanecarboxylic acid 2-(2-aminopropyl)-2,6,7,8-
   tetrahydro-benzo[cd]indazol-4-yl ester;
or combinations thereof.

6. A pharmaceutical composition comprising the compound of claim 1 and at least one carrier.

* * * * *